United States Patent [19]
Koenig et al.

[11] 4,344,891
[45] Aug. 17, 1982

[54] HALOGENATED TERTIARY ALKYL ISOCYANATES AND THEIR PREPARATION

[75] Inventors: Karl-Heinz Koenig, Frankenthal; Volker Schwendemann, Wiesenbach; Karl-Heinz Feuerherd, Ludwigshafen, all of Fed. Rep. of Germany

[73] Assignee: BASF Aktiengesellschaft, Fed. Rep. of Germany

[21] Appl. No.: 185,404

[22] Filed: Sep. 8, 1980

[30] Foreign Application Priority Data

Sep. 13, 1979 [DE] Fed. Rep. of Germany ....... 2937062

[51] Int. Cl.³ ................ C07C 119/042; C07C 119/045
[52] U.S. Cl. ............................ 260/453 A; 260/453 P; 260/453 AL; 260/543 R; 204/158 HA
[58] Field of Search ........ 260/453 A, 453 AL, 453 P, 260/543 R; 204/158 HA

[56] References Cited

U.S. PATENT DOCUMENTS 3,468,923 9/1969 Koenig et al. ............... 260/453 AL
3,535,360 10/1970 Holtschmidt et al. .......... 260/453 P Primary Examiner—Dolph H. Torrence
Attorney, Agent, or Firm—Keil & Witherspoon

[57] ABSTRACT

Halogenated tertiary alkyl isocyanates and a process for their preparation by reacting a tertiary alkyl isocyanate with halogen, sulfuryl chloride and/or sulfuryl bromide.

The halogenated tertiary alkyl isocyanates prepared by the process of the invention are valuable starting materials for the preparation of pest control agents, fatliquoring agents, drugs, flameproofing agents, lubricating oils, synthetic resins and slip agents.

8 Claims, No Drawings

HALOGENATED TERTIARY ALKYL ISOCYANATES AND THEIR PREPARATION

The present invention relates to halogenated tertiary alkyl isocyanates and to a process for their preparation by reacting a tertiary alkyl isocyanate with halogen, sulfuryl chloride and/or sulfuryl bromide.

The halogenation of aliphatic isocyanates possessing one or more replaceable hydrogens on the carbon in the α-position to the nitrogen of the isocyanate group has been disclosed (German Pat. No. 1,122,058, Angew. Chemie, 74 (1962), 848–855 and 80 (1968), 942–953). German Pat. No. 1,122,058 points out that haloalkyl isocyanates are very reactive substances (2nd column, lines 33 and 34) and that α-haloalkyl isocyanates tend to undergo condensation or polymerization (2nd column, lines 30 and 31); Example 3 shows a substantial amount of distillation residues in addition to a 68% yield.

In the absence of solvents, the halogenation of aliphatic isocyanates is often accompanied by resinification due to intramolecular condensation, and by poor yields, as disclosed in Angew. Chemie (loc.cit., page 946). The same publication shows that an addition reaction of the hydrogen chloride, formed during the primary reaction, with the isocyanate results in the formation of large amounts of the corresponding carbamic acid chloride, and recommends that this side-reaction be avoided by using a carbamic acid chloride as the starting material.

If the α-halogenation of aliphatic isocyanates, which is described in German Pat. No. 1,122,058, is carried out on an industrial scale, it is found that on distilling the resulting mixture of halogenated isocyanates of varying degrees of halogenation substantial amounts of non-distillable residues, consisting of polymers or polycondensates, remain, in general amounting to about 20–40% by weight, based on the halogenated product.

We have found that halogenated tertiary alkyl isocyanates of the formula

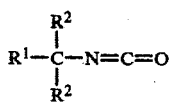

where $R^1$ is $R^2$ or

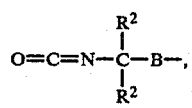

and the individual radicals $R^2$ are identical or different and each is haloalkyl or halogen-free alkyl of 1 to 6 carbon atoms, and two radicals $R^2$ bonded to the same carbon atom may also be members of a halogen-free or halogenated alicyclic ring, B is halogen-free alkylene or haloalkylene of 1 to 6 carbon atoms, and one or more of the radicals $R^2$ possess one or more halogen atoms, are obtained in an advantageous manner by halogenation of isocyanates or carbamic acid chlorides when a tertiary alkyl isocyanate of the formula

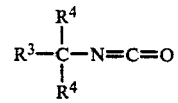

or a tertiary carbamic acid halide of the formula

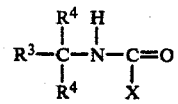

where $R^3$ is $R^4$- or

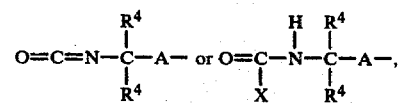

the individual radicals $R^4$ may be identical or different and each is an aliphatic radical having 1 to 6 carbon atoms and two radicals $R^4$ bonded to the same carbon atom may also be members of an alicyclic ring, A is alkylene or haloalkylene of 1 to 6 carbon atoms and X is halogen, is reacted with halogen, sulfuryl chloride and/or sulfuryl bromide.

Further, we have found novel halogenated tertiary alkyl isocyanates of the formula

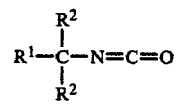

where $R^1$ is $R^2$ or

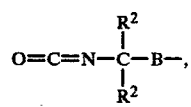

and the individual radicals $R^2$ are identical or different and each is haloalkyl or halogen-free alkyl of 1 to 6 carbon atoms, and two radicals $R^2$ bonded to the same carbon atom may also be members of a halogen-free or halogenated alicyclic ring, B is halogen-free alkylene or haloalkylene of 1 to 6 carbon atoms, and one or more of the radicals $R^2$ possess one or more halogen atoms, and the total number of halogen atoms, if $R^1$ is $R^2$- and all 3 radicals $R^2$ together contain 3 carbon atoms, is not less than 4.

Where tertiary butyl isocyanate and chlorine are used, the reaction is represented by the following equation:

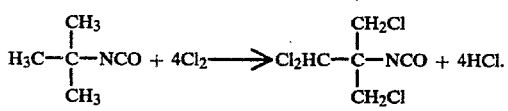

Compared to the prior art, the process according to the invention surprisingly gives halogenated tertiary alkyl isocyanates simply and economically, in good yield and high purity. It was surprising that specifically alkyl isocyanates without a hydrogen atom in the α- position should undergo such an advantageous reaction and produce little or no distillation residues.

Preferred starting materials II and III and accordingly preferred end products I are those where $R^1$ is $R^2$ or is

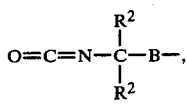

the individual radicals $R^2$ are identical or different and each is halogen-free alkyl or haloalkyl of 1 or 2 carbon atoms or any two radicals $R^2$ bonded to the same carbon atom can, together with this atom, be members of a halogen-free or halogenated alicyclic 5-membered or 6-membered ring, $R^3$ is $R^4$- or

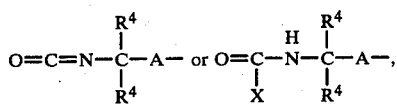

the individual radicals $R^4$ may be identical or different and each is alkyl of 1 or 2 carbon atoms, any two of the radicals $R^4$ bonded to the same carbon atom can, together with this atom, also be members of an alicyclic 5-membered or 6-membered ring, A is alkylene of 1 or 2 carbon atoms, or haloalkylene of 1 or 2 carbon atoms and 1 or 2 halogen atoms, B is halogen-free alkyl of 1 or 2 carbon atoms or haloalkyl of 1 or 2 carbon atoms and 1 or 2 halogen atoms, one or more of the radicals $R^2$ possess one or more halogen atoms, X is bromine or, in particular, chlorine, and each halogen in the end product I is bromine or, in particular, chlorine.

Examples of suitable monoisocyanates II and monocarbamic acid halides III are trimethyl isocyanate, triethyl isocyanate, tripropyl isocyanate, triisopropyl isocyanate, tributyl isocyanate, triisobutyl isocyanate, tri-sec.-butyl isocyanate, tri-tert.-butyl isocyanate, tripentyl isocyanate, triisopentyl isocyanate and trihexylmethyl isocyanate; 1,1-dimethylpropyl isocyanate, 1,1-dimethylbutyl isocyanate, 1,1-dimethylpentyl isocyanate, 1,1-dimethylhexyl isocyanate, 1,1-dimethylheptyl isocyanate and the corresponding 1-ethyl-1-methyl-, 1-propyl-1-methyl-, 1-butyl-1-methyl-, 1-pentyl-1-methyl-, 1-hexyl-1-methyl-, 1-heptyl-1-methyl-, 1,1-diethyl-, 1-ethyl-1-propyl-, 1-ethyl-1-butyl-, 1-ethyl-1-pentyl-, 1-ethyl-1-hexyl- and 1-ethyl-1-isobutyl homologs; 1-propyl-cyclohexyl 1-isocyanate, 1-butyl-cyclohexyl 1-isocyanate, 1-methyl-cyclohexyl 1-isocyanate, 1-ethylcyclohexyl 1-isocyanate, 1-methylcyclopentyl 1-isocyanate and 1-ethylcyclopentyl 1-isocyanate; corresponding substituted carbamic acid chlorides and carbamic acid bromides. Preferred compounds are tert.-butyl isocyanate, tert.-amyl isocyanate, 1,1-dimethylbutyl isocyanate, 1,1-dimethylheptyl isocyanate, 1,1-diethylpropyl isocyanate, 1-methyl-1-ethylpropyl isocyanate and triethylmethyl isocyanate.

Examples of tertiary diisocyanates II and dicarbamic acid halides III which may be used in accordance with the novel process are: 1,1,3,3-tetramethylpropane 1,3-diisocyanate, 1,1,3,3-tetraethylpropane 1,3-diisocyanate, 1,1,3,3-tetraisopropylpropane 1,3-diisocyanate, 1,1,3,3-tetrapropylpropane 1,3-diisocyanate, 1,1,3,3-tetrabutylpropane 1,3-diisocyanate, 1,1,3,3-tetraisobutylpropane 1,3-diisocyanate, 1,1,3,3-tetra-sec.-butylpropane 1,3-diisocyanate, 1,1,3,3-tetra-tert.-butylpropane 1,3-diisocyanate, 1,1,3,3-tetrapentylpropane 1,3-diisocyanate, 1,1,3,3-tetrahexylpropane 1,3-diisocyanate and similarly 1,1-substituted and ω,ω-substituted butane 1,4-diisocyanates, pentane 1,5-diisocyanates, hexane 1,6-diisocyanates, heptane 1,7-diisocyanates and octane 1,8-diisocyanates; homologous diisocyanates with different substituents, from the above group of methyl, ethyl, propyl, isopropyl, butyl, isobutyl, sec.-butyl, tert.-butyl, pentyl, isopentyl and hexyl, in the 1,1-positions and ω,ω-positions, of which substituents 2 or 3 may be identical with one another; 1,2-dicyclohexyl-(1',1")-ethane 1',1"-diisocyanate, dicyclohexyl-(1',1")-methane 1',1"-diisocyanate, 1,3-dicyclohexyl-(1',1")-propane 1',1"-diisocyanate, 1,4-dicyclohexyl-(1',1")-butane 1',1"-diisocyanate and corresponding dicyclopentyl compounds; corresponding dicarbamic acid chlorides, dicarbamic acid bromides and monoisocyanato-monocarbamic acid chlorides and monoisocyanato-monocarbamic acid bromides. Preferred compounds are 1,1,4,4-tetramethyl-butane 1,4-diisocyanate, 1,1,6,6-tetramethyl-hexane 1,6-diisocyanate, 1,4-dimethyl-1,4-di-(isobutyl)-butane 1,4-diisocyanate, 1,6-dimethyl-1,6-di-(isohexyl)-hexane 1,6-diisocyanate, 1,4-dimethyl-1,4-di-(isopropyl)-butane 1,4-diisocyanate, 1,6-dimethyl-1,6-di-(isopropyl)-hexane 1,6-diisocyanate, 1,4-dimethyl-1,4-diethyl-butane 1,4-diisocyanate, 1,6-dimethyl-1,6-diethyl-hexane 1,6-diisocyanate, 1,4-dicyclohexyl-(1',1")-butane 1',1"-diisocyanate and 1,6-dicyclohexyl-(1',1")-hexane 1',1"-diisocyanate.

The starting materials II or III are reacted with halogen, sulfuryl chloride or sulfuryl bromide as the halogenating agent, preferably with iodine or bromine and especially with chlorine. In general, the halogenation gives mixtures of halogenated end products I containing different numbers of halogen substituents. The carbon atoms in the β-position undergo preferential halogenation first. As a rule, the number of halogen substituents per molecule in the main component of the mixture of starting materials I is equal to the molar ratio of halogenating agent to starting material.

The starting materials II or III and the halogenating agent may be employed in the stoichiometric amount; for example, 3 moles of chlorine may be employed per mole of tert.-butyl isocyanate in order to prepare trichloro-tert.-butyl isocyanate. Preferably, an excess of halogenating agent over starting material II or III is used to prepare di-halogenated, trihalogenated and more highly halogenated alkyl isocyanates; the amount used may exceed the stoichiometric amount by up to 15 moles, advantageously by from 0.5 to 8 moles, of halogenating agent per mole of starting material II or III. To prepare substantially monosubstituted compounds, it is advantageous to use less than the stoichiometric amount of halogen, namely up to 0.95 mole, advantageously from 0.6 to 0.9 mole, of halogenating agent per mole of starting material II or III. Preferably, a circulatory halogenation method is used to prepare the more highly halogenated products, in which method unconsumed elementary halogen can be recycled. The excess of halogen can be the lower, the more rapidly the halogen reacts. When using sulfuryl halides, it is advantageous to add a halogenating catalyst, for example catalytic amounts, advantageously from 0.01 to 0.1% by weight based on halogenating agent, of benzoyl peroxide, azo-diisobutyronitrile or ascaridol.

The reaction is preferably carried out with exposure to light, and to generate the light it is preferred to use any light source which emits in the visible region. For example, sunlight or artificial light, eg. from quartz lamps, mercury vapor lamps, daylight lamps or fluorescent tubes, may be used. Preferably, immersed lamps round which the reaction mixture flows are used; in particular, when using a circulatory apparatus, an immersed lamp may be employed in one of the vertical tubes. Light sources which emit a high proportion of radiation in the wavelength range from 3,000 to 5,000 Angström are preferred.

The halogenation temperature is advantageously chosen in accordance with the desired degree of halogenation of the end product I. Thus, if a low degree of halogenation is desired, for example if the starting materials II and III are to be substituted by 1 or 2 halogen atoms, it is advantageous to start the reaction at from 0° to 10° C. and raise the temperature slowly to about 50° C. If a higher degree of halogenation is desired, for example if the starting materials II and III are to be substituted by from 3 to 6 halogen atoms, or if starting material III is used, the reaction is started at from 50° to 100° C. to achieve more rapid uptake of halogen, and the temperature is also raised more rapidly. As the degree of halogenation progresses, it is advantageous to raise the reaction temperature up to at most 230° C., preferably to 160°–180° C., in order to maintain an adequate rate of halogen uptake. As a rule, the reaction is carried out at from −10° C. to 230° C., particularly 40° to 180° C. and preferably from 60° to 180° C., under atmospheric or superatmospheric pressure, continuously or batchwise. Preferably, the reaction is carried out in the absence of an added solvent.

The reaction may be carried out as follows: the starting material II or III is reacted with the halogenating agent at the reaction temperature for from 2 to 50 hours, and if the halogenating agent is an elementary halogen, the latter is added slowly and in portions or continuously over the duration of the reaction. Advantageously, the temperature is raised during the reaction, within the range referred to above and in the manner described above. Where there is only one main product, it is isolated from the reaction mixture in a conventional manner, for example by fractional distillation. However, in the majority of cases, especially in industrial operation, mixtures of end products are obtained, which can be purified by distillation but which are mostly used direct for further conversion, for example for the production of finishing agents, eg. flameproofing agents. The isocyanates with a low degree of halogenation, obtained as first runnings of the distillation, can be re-used, in a subsequent batch, as intermediates for the synthesis of more highly halogenated fractions. The maximum halogen uptake is about 80–85% of theory. The starting materials II are more advantageously used than the starting materials III, since they react more rapidly.

The halogenated tertiary alkyl isocyanates prepared by the process according to the invention are valuable starting materials for the preparation of pest control agents, fatliquoring agents, drugs, flameproofing agents, lubricating oils, synthetic resins and slip agents. For example, the chlorinated monoisocyanates may be used to block the end groups of hydroxyl-containing polymers, and the polychlorinated diisocyanates may be used direct as bifunctional reactants in the synthesis of flameproof polymers, for example polyurethanes. Regarding the use of the compounds, reference may be made to the publications cited earlier.

In the Examples which follow, parts are by weight.

EXAMPLE 1

Chlorine is passed into 90 parts of tert.-butyl isocyanate at 2° C., under irradiation from a fluorescent tube (4,000–7,000 Angström). Whilst the chlorine is being taken up, the temperature is gradually raised to 95° C. over 3 hours. When 126 parts of chlorine have been taken up, the mixture obtained is subjected to fractional distillation. The chlorine uptake corresponds to the substitution of about 4 hydrogen atoms. 48 parts of first runnings consisting of isocyanates with a low degree of halogenation (which fraction has a boiling point of 100°–116° C./27 mbar and is re-used in a subsequent chlorination batch), 70 parts of tetrachloro-t-butyl isocyanate (boiling point 119°–130° C./27 mbar) and 65 parts of a mixture of pentachloro-t-butyl isocyanate and hexachloro-t-butyl isocyanate (boiling point 60°–73° C./0.13 mbar) are obtained.

EXAMPLE 2

Elementary chlorine is passed into 40 parts of 1,1,4,4-tetramethylbutane 1,4-diisocyanate at 50° C., under illumination from a fluorescent tube (4,000–7,000 Angström), the reaction temperature being slowly raised to 180° C. over 6 hours. 62 parts of chlorine are taken up. This corresponds to a substitution of about 8 hydrogen atoms. The oily product is subjected to fractional distillation, and the following fractions are obtained:

(a) Boiling point 54°–180° C./0.27 mbar: 18.5 parts of halogenated 1,1,4,4-tetramethylbutane 1,4-diisocyanate (3 chlorine atoms per molecule).

(b) Boiling point 130°–160° C./0.133 mbar: 21 parts of halogenated 1,1,4,4-tetramethylbutane 1,4-diisocyanate (6 chlorine atoms per molecule).

(c) Boiling point 167°–190° C./0.133 mbar: 40 parts of halogenated 1,1,4,4-tetramethylbutane 1,4-diisocyanate (10 chlorine atoms per molecule).

EXAMPLE 3

Elementary chlorine is passed into 120 parts of tert.-butyl isocyanate at 10° C., under illumination from a fluorescent tube (4,000–7,000 Angström). Whilst the chlorine is being introduced, the reaction temperature is slowly raised to 160° C. over 4 hours. After 90 parts of chlorine gas have been taken up, the solution is flushed with dry nitrogen and the mixture is subjected to fractional distillation under reduced pressure. The following fractions are obtained:

(d) Boiling point 86°–118° C./24 mbar: 25 parts of halogenated tert.-butyl isocyanate (3 chlorine atoms)

(e) Boiling point 64°–74° C./0.27 mbar: 70 parts of halogenated tert.-butyl isocyanate (5 chlorine atoms)

(f) Boiling point 86°–97° C./0.27 mbar: 96 parts of a mixture of 80% by weight of 1-(trichloromethyl)-1-(dichloromethyl)-2-chloroethyl isocyanate and 20% by weight of 1,1-bis-(dichloromethyl)-2,2-dichloroethyl isocyanate.

EXAMPLE 4

Instead of tert.-butyl isocyanate, 164 parts of crude tert.-butylcarbamyl chloride, as obtained by phosgenating tert.-butylamine, are used. The reaction is carried out similarly to Example 3, the chlorination being started at 80° C. The following fractions are obtained:

(g) Boiling point 86°–118° C./24 mbar: 25 parts of halogenated tert.-butyl isocyanate (3 chlorine atoms)

(h) Boiling point 64°–74° C./0.27 mbar: 70 parts of halogenated tert.-butyl isocyanate (5 chlorine atoms)

(i) Boiling point 86°–97° C./0.27 mbar: 96 parts of a mixture of 80% by weight of 1-(trichloromethyl)-1-(dichloromethyl-2-chloroethyl isocyanate and 20% by weight of 1,1-bis-(dichloromethyl)-2,2-dichloroethyl isocyanate.

EXAMPLE 5

951 parts of the low-halogen fractions d and e of Example 3 are added to 844 parts of t-butyl isocyanate, and chlorine is introduced into the mixture, initially at 30°–40° C., under irradiation from an immersed ultraviolet lamp. The exothermic reaction is allowed to proceed, with continued introduction of chlorine, until the temperature reaches 100° C. As the amount of chlorine taken up increases, external heating (up to 135° C.) is finally necessary. After a weight increase of 1,714 parts (=24 moles), excess dissolved hydrogen chloride is flushed out with dry nitrogen at 120° and the residue is then subjected to fractional distillation under reduced pressure. The following fractions are obtained on distillation through a 30 cm packed column:

| Fractions: | | | |
|---|---|---|---|
| 1. Boiling point at 0.1 mbar | 45–49° | 190 parts | $n_D^{25} = 1.5096$ |
| 2. Boiling point at 0.1 mbar | 49–54° | 163 parts | $n_D^{25} = 1.5180$ |
| 3. Boiling point at 0.1 mbar | 54–55° | 185 parts | $n_D^{25} = 1.5209$ |
| 4. Boiling point at 0.1 mbar | 55–57° | 190 parts | $n_D^{25} = 1.5220$ |
| 5. Boiling point at 0.1 mbar | 57° | 183 parts | $n_D^{25} = 1.5230$ |
| 6. Boiling point at 0.1 mbar | 57–60° | 181 parts | $n_D^{25} = 1.5243$ |
| 7. Boiling point at 0.1 mbar | 60–62° | 167 parts | $n_D^{25} = 1.5258$ |
| 8. Boiling point at 0.1 mbar | 62–66° | 245 parts | $n_D^{25} = 1.5279$ |
| 9. Boiling point at 0.1 mbar | 66–85° | 447 parts | crystalline |
| 10. Boiling point at 0.1 mbar | 85–88° | 390 parts | crystalline |

Distillation residue: about 75 parts.

All fractions from fraction 5. inclusive contain isomer mixtures with 6 chlorine atoms, and in the case of fractions 9 and 10, small proportions with 7 chlorine atoms, per mole of tert.-butyl isocyanate (67.5–70.9% of chlorine). The main component in fraction 10 is 1-(trichloromethyl)-1-(dichloromethyl)-2-chloroethyl isocyanate.

Fractions 1–4 can be reused for chlorination.

EXAMPLE 6

47 parts of 1,1,2-trimethylpropyl isocyanate are chlorinated, starting at 0°, and using a laboratory lamp attached to the exterior of the flask. The exothermic reaction raises the temperature to about 120°. The total weight increase, after continuing the reaction at 130°, is 66 parts (=0.93 mole). After flushing out the dissolved hydrogen chloride, the product is fractionated under reduced pressure from an oil pump:

| | | O | N | Cl |
|---|---|---|---|---|
| B.p./0.1 mbar 49–50° - 9 parts | $n_D^{20} = 1.5276$ | 5.1 | 4.3 | 61.7 |
| B.p./0.1 mbar 102–110° - 16 parts | $n_D^{20} = 1.5454$ | 4.9 | 4.4 | 61.9 |
| B.p./0.1 mbar 110–5° - 22 parts | $n_D^{20} = 1.5461$ | 4.8 | 4.3 | 63.0 |
| B.p./0.1 mbar 115–7° - 23 parts | $n_D^{20} = 1.5491$ | 4.7 | 4.0 | 64.6 |
| B.p./0.1 mbar 117–25° - 18 parts | $n_D^{20} = 1.5571$ | 4.8 | 4.2 | 63.8 |

There are 5 parts of distillation residue.
Calculated for $C_7H_7ONCl_6$, O = 4.8 N = 4.2 chlorine 63.8.

EXAMPLE 7

120 parts of 1,5-dimethyl-1-ethyl-hexyl isocyanate are chlorinated in a similar manner to Example 5. 90 parts of the colorless, viscous oil obtained ($n_D^{22} = 1.5320$) are fractionally distilled:

| B.p./0.2 mbar | 36–165° - 3 parts | $n_D^{22} = 1.5195$ |
|---|---|---|
| B.p./2.5 mbar | 165–175° - 7 parts | $n_D^{22} = 1.5215$ |
| B.p./1.0 mbar | 175–80° - 15 parts | $n_D^{22} = 1.5255$ |
| B.p./2.0 mbar | 180–184° - 20 parts | $n_D^{22} = 1.5295$ |
| B.p./2.0 mbar | 184–187° - 17 parts | $n_D^{22} = 1.5368$ |

According to the O, N and chlorine analyses fractions 2 and 3 contain in the main 5 chlorine atoms and fractions 4 and 5 particularly 6 chlorine atoms, per isocyanate molecule.

EXAMPLE 8

Addition reaction of chlorine, followed by substitution.

First, 82 parts of elementary chlorine are caused to undergo addition to 64 parts of 1-methylbut-2-ynyl isocyanate whilst cooling the mixture in an ice bath, the actual reaction temperature being about 20° C. 1-Methyl-3,4-tetrachlorobut-2-yl isocyanate, a colorless product, distils at 63°–64°/0.1 mbar; $n_D^{22} = 1.5070$.

This product is further chlorinated, as described in Example 6, with elementary chlorine at 80°–120°, until the weight has increased by 39 parts. Fractional distillation of the product, without a column, gives a small amount of first runnings, and then the following fractions:

| B.p./0.1 mbar | 62–70° - 16 parts | $n_D^{24} = 1.5240$ |
|---|---|---|
| B.p./0.1 mbar | 75–100° - 12 parts | $n_D^{24} = 1.5450$ |
| B.p./0.1 mbar | 103–15° - 63 parts | $n_D^{24} = 1.5540$ |
| B.p./0.1 mbar | 115–29° - 29 parts | $n_D^{24} = 1.5600$ |

According to NMR analysis and determination of isocyanate groups, O, N, and chlorine, the main fractions, i.e. the last two fractions, contain 7 chlorine atoms per molecule, the principal product being 1-dichloromethyl-2-chloromethyl-3,4-dichlorobut-2-yl isocyanate.

EXAMPLE 9

214 parts (1.34 moles) of bromine are added dropwise to 100 parts (0.67 mole) of 1-(ethynyl)-cyclohex-1-yl isocyanate at 20°. The resulting 1-(tetrabromoethyl)-cyclohex-1-yl isocyanate (boiling point 118–22°/0.2 mbar, $n_D^{23} = 1.5611$) serves as the starting material for the product described below, which is an isocyanate containing a mixture of halogens.

90 parts of the above 1-(tetrabromoethyl)-cyclohex-1-yl isocyanate, dissolved in 180 parts of tetrachloroethane, are exposed to ultraviolet light and chlorinated initially at 50°–90° and finally at the boil, until 26 parts of chlorine have been taken up. The solution, whilst still hot, is flushed with the dry nitrogen, which removes yellowish brown vapors. The solvent is then stripped off under reduced pressure and finally the residue is subjected to fractional distillation.

| B.p./0.2 mbar | 108–135° (first runnings) | 4 parts | $n_D^{20} = 1.5729$ |
|---|---|---|---|
| B.p./0.2–0.5 mbar | 135–146° | 12 parts | $n_D^{20} = 1.5750$ |

| B.p./0.5 mbar 144–146° | 54 parts | $n_D^{20} = 1.5772$ |

3 parts of residue are left.

The main fraction gives the following analytical results:

O=4.2%; N=3.2%; Br=31.4%; Cl=28.7%.

We claim:

1. A process for the preparation of halogenated tertiary alkyl isocyanates of the formula

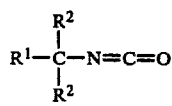     I where $R^1$ is $R^2$ or

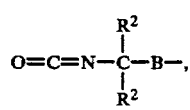

and the individual radicals $R^2$ are identical or different and each is haloalkyl or halogen-free alkyl of 1 to 6 carbon atoms, and two radicals $R^2$ bonded to the same carbon atom may also be members of a halogen-free or halogenated alicyclic ring, B is halogen-free alkylene or haloalkylene of 1 to 6 carbon atoms, and one or more of the radicals $R^2$ possess one or more halogen atoms, by halogenation of isocyanates or carbamic acid chlorides, wherein a tertiary alkyl isocyanate of the formula

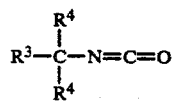     II or a tertiary carbamic acid halide of the formula

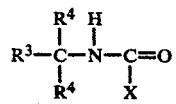     III where $R^3$ is $R^4$- or

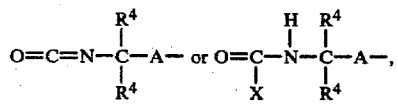

the individual radicals $R^4$ may be identical or different and each is an aliphatic radical having 1 to 6 carbon atoms and two radicals $R^4$ bonded to the same carbon atom may also be members of an alicyclic ring, A is alkylene or haloalkylene of 1 to 6 carbon atoms and X is halogen, is reacted with halogen, sulfuryl chloride and/or sulfuryl bromide.

2. A halogenated tertiary alkyl isocyanate of the formula

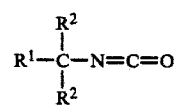     I where $R^1$ is $R^2$ or

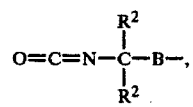

and the individual radicals $R^2$ are identical or different and each is haloalkyl or halogen-free alkyl of 1 to 6 carbon atoms, and two radicals $R^2$ bonded to the same carbon atom may also be members of a halogen-free or halogenated alicyclic ring, B is halogen-free alkylene or haloalkylene of 1 to 6 carbon atoms, and one or more of the radicals $R^2$ possess one or more halogen atoms, and the total number of halogen atoms, if $R^1$ is $R^2$- and all 3 radicals $R^2$ together contain 3 carbon atoms, is not less than 4.

3. A process as defined in claim 1, wherein the reaction to prepare dihalogenated, trihalogenated and more highly halogenated alkyl isocyanates is carried out with an excess, over the stoichiometric amount, of up to 15 moles of halogenating agent per mole of starting material II or III.

4. A process as defined in claim 1, wherein the reaction for the preparation of substantially monosubstituted compounds is carried out with less than the stoichiometric amount of halogenating agent, namely with up to 0.95 mole per mole of starting material II or III.

5. A process as defined in claim 1, wherein, when using sulfuryl halides, the reaction is carried out with catalytic amounts of a halogenating catalyst, namely with from 0.01 to 0.1% by weight, based on the halogenating agent.

6. A process as defined in claim 1, wherein the reaction is carried out under exposure to light in the wavelength range of from 3,000 to 5,000 Ångström.

7. A process as defined in claim 1, wherein the reaction is carried out at from 0° to 230° C.

8. A process as defined in claim 1, wherein the reaction is carried out at from 60° to 180° C.

* * * * *